United States Patent [19]

Sterling

[11] Patent Number: 4,578,413
[45] Date of Patent: * Mar. 25, 1986

[54] POLYMERIC TUBINGS COMPRISING POLYSILOXANE-MODIFIED ELASTOMER COMPOSITIONS

[75] Inventor: Robert E. Sterling, New Port Richey, Fla.

[73] Assignee: Medical Research Associates, Ltd. #2, Clearwater, Fla.

[*] Notice: The portion of the term of this patent subsequent to Nov. 6, 2001 has been disclaimed.

[21] Appl. No.: 563,825

[22] Filed: Dec. 21, 1983

[51] Int. Cl.$^4$ .................. C08L 25/10; C08L 9/06; A01N 1/00
[52] U.S. Cl. .................. 524/269; 523/112; 524/267; 604/93
[58] Field of Search ............ 524/267, 269; 523/112

[56] References Cited

U.S. PATENT DOCUMENTS

| | | | |
|---|---|---|---|
| 2,655,489 | 10/1953 | Lawson | 260/29.1 |
| 2,888,419 | 5/1959 | Safford | 260/29.1 |
| 2,992,201 | 7/1961 | Gober, Jr. | 260/29.1 |
| 3,239,478 | 3/1966 | Marlan, Jr. | 260/27 |
| 3,272,766 | 9/1966 | Gowman | 260/17 |
| 3,441,530 | 4/1969 | Bauer et al. | 260/28.5 |
| 3,445,420 | 5/1969 | Kookootsedes et al. | 260/37 |
| 3,459,831 | 8/1969 | Luftglass et al. | 260/876 |
| 3,485,787 | 12/1969 | Hacfele et al. | 260/33.6 |
| 3,576,913 | 4/1971 | Johnson et al. | 260/880 |
| 3,766,295 | 10/1973 | Crossland et al. | 260/829 |
| 3,795,646 | 3/1974 | MacKenzie, Jr. et al. | 260/29.15 B |
| 3,817,248 | 6/1974 | Buckles et al. | 128/260 |
| 3,830,767 | 8/1974 | Condon | 260/28.5 B |
| 3,865,766 | 2/1975 | Merrill | 260/185 |
| 3,896,815 | 7/1975 | Fettel et al. | 128/348 |
| 3,919,157 | 11/1975 | Ide et al. | 260/29.7 T |
| 3,962,519 | 6/1976 | Ruesch et al. | 524/269 |
| 4,006,116 | 2/1977 | Dominguez | 260/33.6 AQ |
| 4,039,629 | 8/1977 | Himes et al. | 260/876 B |
| 4,041,103 | 8/1977 | Davison et al. | 260/857 D |
| 4,049,595 | 9/1977 | Dominquez | 260/5 |
| 4,108,825 | 8/1978 | Hayes | 260/375 B |
| 4,123,409 | 10/1978 | Kaelble | 260/29.15 B |
| 4,143,651 | 3/1979 | Patel | 128/349 B |
| 4,157,094 | 6/1979 | Patel | 428/349 B |
| 4,196,731 | 4/1980 | Laurin et al. | 128/214 R |
| 4,198,983 | 4/1980 | Becker et al. | 128/349 R |
| 4,481,323 | 11/1984 | Sterling | 524/269 |

Primary Examiner—Herbert S. Cockeram
Attorney, Agent, or Firm—Sherman and Shalloway

[57] ABSTRACT

This invention provides tubings formed of a polymeric composition comprising a thermoplastic elastomeric hydrocarbon black copolymer and a polysiloxane having a kinematic viscosity of 20 to $10^6$ centistokes at room temperature, the polysiloxane constituting from about 0.1 to 12 percent by weight of the composition. The tubings can be used in medical applications.

21 Claims, 4 Drawing Figures

U.S. Patent  Mar. 25, 1986  Sheet 1 of 2  4,578,413
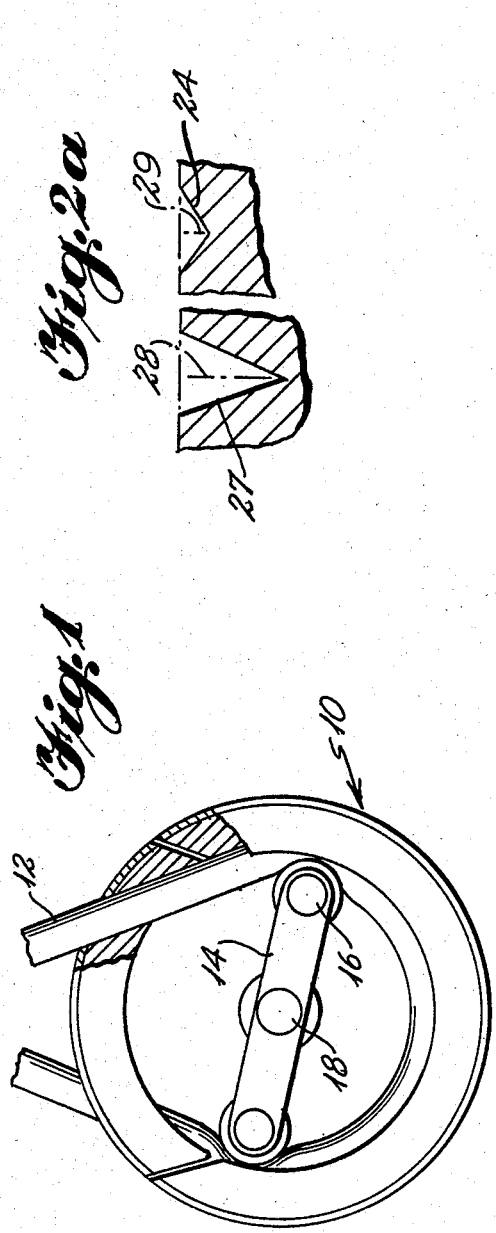
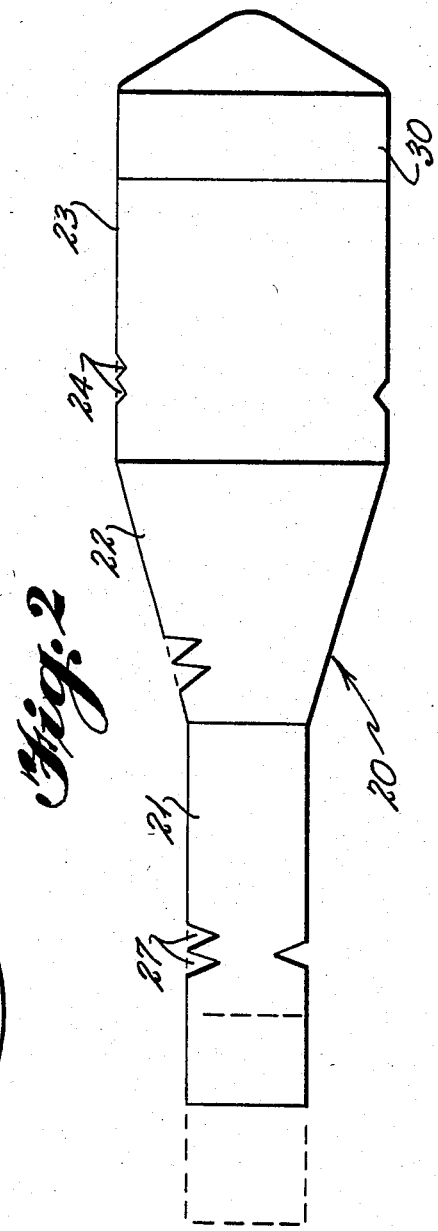

POLYMERIC TUBINGS COMPRISING POLYSILOXANE-MODIFIED ELASTOMER COMPOSITIONS

BACKGROUND OF THE INVENTION

1. Field of the Invention

This invention relates to polymeric tubings and more particularly to medical grade tubings for clinical use.

2. Description of the Prior Art

The use of polymeric tubings in medical or clinical applications is well known. In general, such tubings are made of natural or synthetic polymeric materials. Since the tubings come in contact with human tissues or body fluids, stringent requirements must be met for medical applications. These requirements vary, depending on the nature of the application.

Numerous techniques have been developed to assist or replace the failing heart. The methods of assistance utilized vary with the degree and duration of ventricular dysfunction. In general, the most common type of cardiac assistance comprises pumping the blood from the patient, feeding the blood to an oxygenator and returning the oxygenated blood back to the patient. The pump most commonly used is a roller pump.

FIG. 1 shows a typical roller pump 10 where a tubing 12 is compressed by a rotating arm 14 having a roller 16 at each end. Rotating arm 14 which rotates about hub 18 exerts gentle mechanical action on the blood so as not to damage the blood.

It is evident that in selecting the tubing material for use in a roller pump several physical characteristics for the material must be considered carefully. Such characteristics include: (1) rebounding of tubing (volume vs revolutions per minute); (2) rebounding over time with continuous pumping; (3) flex life; and (4) spallation (i.e. tubing debris produced by pumping). Among these, spallation is particularly important in that for obvious reasons the production of debris as a result of pumping should be kept to a minimum so as to avoid the introduction of foreign matters into the patient's blood.

The materials most commonly used in the production of medical grade tubings include polyvinyl chloride, silicone rubber and synthetic rubber. However, these materials have been found to be unsatisfactory in that they either have short flex life or high spallation. Hence, there is a need for a polymeric material which possesses long flex life and low spallation for the manufacture of medical grade tubings, particularly tubings useful in cardiac assistance equipment.

BRIEF DESCRIPTION OF THE DRAWINGS

FIG. 1 illustrates a conventional roller pump.

FIG. 2 illustrates an extruder screw for applying shearing pressure to the polymeric composition in forming tubings.

FIG. 2A shows the cross-sectional areas of the flights in the extruder screw.

SUMMARY OF THE INVENTION

Figure 4:
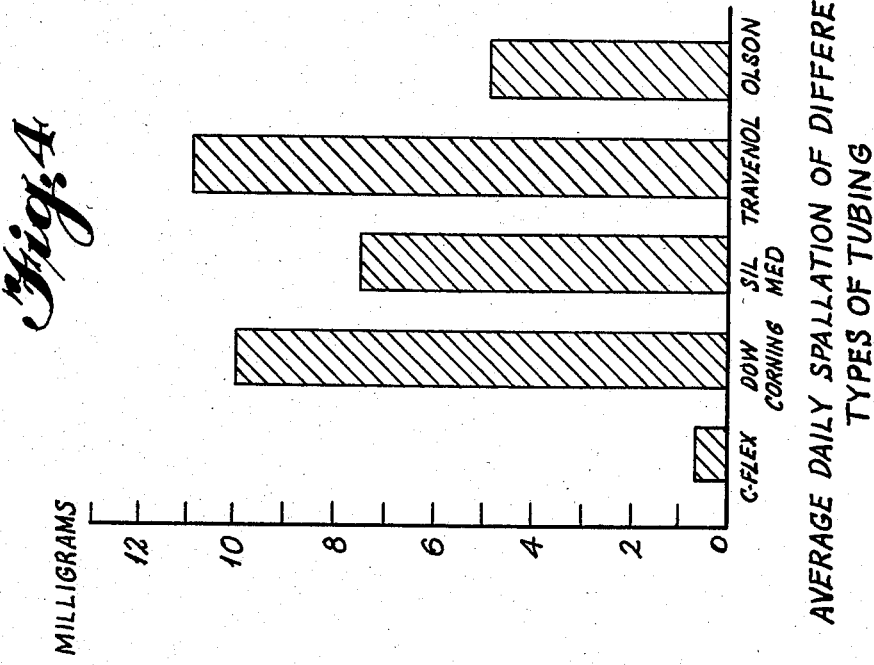
FIG. 4 shows the spallation of the tubings tested in Example 5.

The present invention provides tubings formed of a polymeric composition comprising a thermoplastic elastomeric hydrocarbon block copolymer and a polysiloxane. The block copolymer comprises blocks of styrene-ethylene-butylene-styrene wherein the styrene blocks have a molecular weight of 5,000 to 40,000 and the ethylene-butylene block, 20,000 to 500,000. Mineral oil and polypropylene can be incorporated in the composition. The polysiloxane has a kinematic viscosity of 20 to $10^6$ centistokes at room temperature. Tubings having such a composition are useful as medical grade tubings and particularly as tubings in cardiac assistance applications.

DETAILED DESCRIPTION OF THE INVENTION

The present invention provides tubings formed of a composition comprising a substantially uniform mixture of an elastomeric thermoplastic hydrocarbon block copolymer and a polysiloxane. The composition, which may contain more than one hydrocarbon block copolymer, possesses physical and surface properties which avoid all of the above-described problems found in conventional medical grade tubing materials. The present tubings have been found to possess high flex life and extremely low spallation.

In its simplest form, the composition comprises from about 0.1 to 12 percent, by weight, of the polysiloxane, the remainder being the block copolymer. This represents an unusual result primarily because of the dissimilar nature of the polysiloxane molecule compared to the hydrocarbon backbone of the elastomeric macromolecule.

The polysiloxane content of the composition becomes even more unusual where the latter includes an appreciable amount of mineral oil. In fact, the mineral oil may even represent 60 percent of the composition's total weight. Nonetheless, the composition appears able to take up an appreciable amount of polysiloxane and achieve the beneficial results.

The composition may include other additives such as polypropylene, generally in an amount less than 45 percent of the total weight of the composition. In addition, antioxidants may be included in the composition.

The block copolymer which preferably comprises from about 23 to 73 percent by weight of the total weight of the composition may have an A—B, preferably A—B—A, configuration in which A takes the form of a monovinyl arene polymer block. To provide the elastomeric properties, B may be a hydrogenated or nonhydrogenated conjugated diene polymer block. The copolymer may contain more than two or three blocks suggested above. It may have several interspersed A and B blocks linearly interconnected as A—B—A—B—A—B. Alternately or additionally, the block copolymer may have blocks with a branched connection to the main chain as

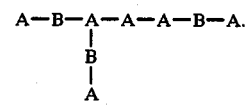

For the present invention, the A—B—A structure will be used to encompass all of these variations in polymer block structure.

The styrene-ethylene-butylene-styrene macromolecule represents a prime example of this type of block copolymer, wherein the styrene blocks typically constitute about 20 to 50 percent of the copolymer's weight while the ethylene-butylene block provides the remaining 50 to 80 percent. The styrene blocks themselves normally have a molecular weight in the range of 5,000 to 40,000. The ethylene-butylene block has a molecular weight greatly exceeding that of the styrene blocks and falling within the approximate range of 20,000 to 500,000. The total molecular weight of the copolymer typically ranges from 50,000 to 600,000.

When more than one block copolymer is used to prepare the polymeric composition, the block copolymers have different contents of terminal A blocks and middle B blocks.

The polysiloxane, which is an essentially linear polysiloxane, has a kinematic viscosity within the range of about 20 to $10^6$, preferably about 200 to 13,000, centistokes at room temperature (20° to 25° C.). A typical example of the polysiloxane is silicone oil. The polysiloxane has the repeating structure:

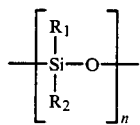

wherein $R_1$, $R_2$ = H, CH$_3$, or

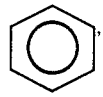

with CH$_3$ being preferred, and n is a positive integer having a value ranging from 10 to 20,000.

Examples of such block copolymers are described in a series of U.S. patents issued to the Shell Chemical Company namely: U.S. Pat. Nos. 3,485,787; 3,830,767; 4,006,116; 4,039,629; and 3,041,103.

Adding a polysiloxane, preferably silicone oil, to one or more elastomeric, thermoplastic hydrocarbon block copolymers accomplishes several distinct and desirable results. Initially, the composition displays a substantial improvement in its processability. This has particular importance when the material is formed into thin webs. Without the polysiloxane, the material appears to have flow and surface properties which cause the molten plastic to form globules, thus a rough surface.

The surface effects produced by the polysiloxane appear to derive from a slightly increased concentration of silicone molecules at the composition's surface. The processing techniques discussed below should typically result in a uniform dispersement of the polysiloxane throughout the composition. However, a slight migration of the silicone molecules to the material's surface occurs. As a result, the material's surface, to a depth of about 5.0 to 20.0 nm., appears to have a concentration of silicone molecules approximately twice that of the bulk of the material. The thinness of this layer, of course, prevents the greater concentration there from affecting the bulk concentration of the polysiloxane throughout the material. Consequently, on a macroscopic scale, the material has a substantially uniform dispersement of the polysiloxane. This gives the surface substantially different properties than the hydrocarbon block copolymer without the polysiloxane.

Both the surface smoothness and concentration of polysiloxane portend a blood compatibility of the material. Both factors reduce the likelihood of the attachment and clotting of blood components to the polymer.

Typically, the middle or B, block of the A—B—A elastomeric hydrocarbon block copolymer provides the molecule with its elastomeric properties; the B blocks themselves possess the rubber qualities. Polymers formed from conjugated dienes have found favor in this role. Butadiene and isoprene represent monomers which, after polymerization, have provided the middle, elastomeric block. Furthermore, the butadiene block may undergo hydrogenation to become an ethylene-butylene copolymer elastomeric block.

The resulting block copolymer typically has its mechanical properties determined primarily by the elastomeric B block. Accordingly, the middle block should provide at least a majority of the block copolymer's total molecular weight. In fact, it usually provides 50 to 80 percent of the molecular weight of the final product. The molecular weight of the middle B block usually falls within the range of 20,000 to 500,000 and typically comes within the narrower range of 20,000 to 200,000.

The terminal, or A, blocks of the copolymer provide the cohesiveness between the individual macromolecules in the thermoplastic rubber. These terminal blocks themselves behave as a thermoplastic. They do not usually diaplay any elastomeric quality. However, representing a minority of the weight of the final elastomer, they do not impart their own mechanical properties to the product.

The thermoplastic adherence between molecules of the A blocks replaces the vulcanization of the natural, latex, or silicone rubbers. In vulcanization, actual chemical bonds develop between the macromolecules constituting the rubber. These crosslinking reactions generally occur at elevated temperatures and thus impart the name "thermoset" to the materials. These rubbers generally require extensive periods of time to "cure": or undergo the required crosslinking. The crosslinking does not represent a reversable process. As a consequence, the nonthermoplastic rubbers, once cured to a particular form, cannot melt to adopt a different form. At elevated temperatures they only oxidize or, in more extreme cases, burn.

The terminal A blocks of the block copolymer adhere to each other through physical attraction bonds characteristic of all thermoplastics. Thus, when in the solid form, the terminal blocks of several molecules adhere to each other to provide the required cohesiveness throughout the material. These particles serve to bind the sundry macromolecules in the mass into an integral whole.

At elevated temperatures, these "particles" of physically bonded terminal blocks of different macromolecules actually melt. The entire mass of material then assumes the liquid or molten state and can undergo the usual processing techniques such as injection molding. When cooled, the terminal blocks of different macromolecules again physically bond to each other and form particles. The material then generally retains the shape it possessed when the particles formed by the terminal A blocks coalesced into the solid state.

The class of molecules labeled monovinylarenes have provided suitable thermoplastic terminal A blocks for these polymers. Examples of the monomers which can polymerize into the terminal blocks include isoprene and alphamethyl isoprene. The former of these two has generally received greater use.

The terminal A blocks generally have a molecular weight within the range of 5,000 to 40,000, and most fall within the range of 8,000 to 20,000. The terminal blocks constitute about 20 to 50 percent of the total weight of the macromolecule.

As discussed above, the elastomeric block copolymer molecule may include more than two or three blocks suggested by the A—B—A formula. The macromolecule may contain additional blocks arranged in either the linear or branched fashion. In this eventuality, the thermoplastic A block may not actually represent the terminal blocks at all ends of the molecule. In any event, the macromolecule generally has a total molecular weight falling within the range of 50,000 to 600,000.

As mentioned previously, one or more of the block copolymers may be used in forming the composition. When more than one block copolymer is used, the block copolymers differ from each other with respect to the amounts of terminal A blocks and middle B blocks present therein. For instance, a mixture of a first block copolymer containing about 28 percent by weight styrene block A (e.g., Shell Kraton G 1650) and a second block copolymer containing about 33 percent by weight styrene block A (e.g., Shell Kraton G 1651) can be used. The weight ratio of the first:second block copolymer can vary from 15:85 to 50:50

The polysiloxane has the following repeating structure:

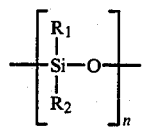

where $R_1$, $R_2$ = H, $CH_3$, or

and n is a positive integer between 10 and 20,000. The readily available silicone oils generally employ the methyl group for both of the radicals $R_1$ and $R_2$. The polysiloxane is essentially linear as shown in the above formula. A preferred example of the polysiloxane is silicone oil.

The viscosity of the polysiloxane should permit the facile coating of and mixing with the crumbs or pellets of the elastomer. This results in a general requirement that the kinematic viscosity within the range of about 20 to 1,000,000 centistokes. At the lower end of the above range, the polysiloxane encounters some difficulty in coating the polymer pellets. As a preferred embodiment, silicone oil having a kinematic viscosity of 200 to 13,000 centistokes works well without complication.

For the present tubings, a medical grade polysiloxane should be employed. Furthermore, devolatilizing the polysiloxane prior to its introduction to the block copolymer removes very low molecular weight elements that could leach and irritate the patient's tissues.

The polysiloxane generally constitutes about 0.1 to 12 percent of the total weight of the elastomeric composition, preferably from 1 to 7 percent. The ability of the hydrocarbon to take up this amount of the polysiloxane is surprising; the hydrocarbon backbone of the polymer has a drastically disparate nature as compared to the silicone structure of the polysiloxane.

The surprise becomes even greater for polymeric compositions that already include substantial amounts of mineral oil as a lubricant. Mineral oil, if present, may account for up to 60 percent of the total weight of the composition. Typically, the mineral oil constitutes from 25 to 50 percent of the composition's total weight.

Furthermore, the mineral oil and the polysiloxane also have distinctly different chemical properties. The former has a hydrocarbon composition as compared to the silicone of the polysiloxane. Moreover, the mineral oil fills the spaces that would presumably accommodate the polysiloxane. Yet, a composition having 50 percent of mineral oil can still assimilate several percent of the polysiloxane to produce a drastically different elastomer.

Adding polypropylene as a binder to the present elastomeric composition produces a stiffening effect upon the elastomeric composition The polypropylene also reduces its elasticity slightly. The amount of added polypropylene generally remains less than 45 percent of the composition's total weight. It more usually falls within the range of 2 to 20 percent or in the narrower range of 5 to 10 percent. The addition of bismuth provides the polymeric composition with an opacity to X-rays. Titanium dioxide pigment can also be added to affect the polymer's visual appearance.

The following represents a summary of the weight percentages of the components in the present polymeric composition.

| Component | Weight % Broad | Preferred |
|---|---|---|
| Polysiloxane | 0.1–12 | 1–7 |
| Polypropylene | 0–45 | 1–20 |
| Mineral Oil | 0–60 | 25–50 |
| Block copolymer | balance to 100% | 23–73 |

Preparing the elastomeric composition with the dispersed polysiloxane begins with the hydrocarbon block copolymer. The techniques for preparing the elastomeric thermoplastics appear in many references including the patents referenced above. The inclusion of the usual additives also appears in these discussions.

Mixing the crumbs or pellets of one or more of the elastomeric copolymers, having different amounts of the constituent blocks, with the polysiloxane should result in a coating of the former with the latter. To do so, the pellets or crumbs and the polysiloxane may be mixed in a tumbler. Any additional ingredients, such as polypropylene, polystyrene, and/or stabilizer may also be added to the mixture at this point.

The coated elastomer pellets or crumbs next receive sufficient heat to induce their melting. Applying a shearing pressure to the melted coated crumbs or pellets appears to induce a substantially uniform dispersement of the polysiloxane in the mixture. The heat required to effectuate the melting, of course, depends upon the individual elastomer. Typically, it ranges from 160° C. to 225° C.

After melting the block copolymer by heating, the mixture comprising the block copolymer, the polysiloxane and other suitable ingredients described above may be optionally fed through a plurality of calender rolls to form sheets of the mixture. Thereafter, the sheets are subjected to shearing pressure by feeding the cut strips of sheets to an extruder or a compression molding machine for better dispersement of the polysiloxane.

To ensure adequate dispersement of the polysiloxane, the composition is subjected to an appropriate amount of pressure, usually about 1,500 p.s.i. However, it has been found that by increasing the pressure, further improved properties of the product are obtained. Thus, the molten mixture may be subjected to pressures of 2,500 p.s.i., 3,000 p.s.i., or higher.

An extruder provides the most convenient means of achieving the temperatures and pressures required to disperse the polysiloxane within the composition. An extruder typically has several temperature zones and thus can pass the crumbs or pellets of the polymer through the temperature stages required for melting. FIG. 2 shows an extruder screw generally at 20 modified to apply a greater shearing pressure to the resin material.

The screw 20 has the four zones characteristic of most extruder screws. The first section 21, known as the feed zone, initiates the melting of the polymer pellets and moves them along to the compression or transition zone 22. In zone 22, the polymer generally completely melts and undergoes a sufficient shearing stress to cause thorough mixing of the ingredients. The metering section 23 usually provides the melted resin to the die at a known rate and pressure. Working section 30 allows mixing of the polymer melt.

The screw shown in FIG. 2 has a length-to-diameter ("L/D") ratio of 24:1. In this type of screw, the metering section 23 typically has about 20 to 25 percent of the total flights, or pitch lengths, of the entire screw. On the modified screw 20 shown in FIG. 2, the metering section 23 has ten flights 24 of the screw's total of 24.62 flights; the feed section 21 has 6.62 flights 27, and the transition section 22 has eight flights. Thus, for the screw 20, the metering section 23 has 40 percent of the total flights. This large fraction of the flights increases the length of time that the resin remains in the metering section 23 and the amount of pressure applied to it.

Furthermore, as shown in FIG. 2a, the flights 24 of the metering section 23 have a much smaller cross-sectional area than the flights 27 of the feed section 21. In fact, the depth 28 of the feed-section flight 27 amounts to four times the depth 29 of the metering-section flight 24. This high compression ratio of 4:1 drastically increases the pressure applied to the material in the metering section 23. To increase the pressure even further, the compression ratio of the feed-section flights 21 to those in the metering section 23 may even go to 5:1 or higher. As this ratio increases, the material becomes squeezed into the smaller flights 24 and, thus, experiences a greater shearing pressure.

Naturally, the pressure experienced by the polymer in the flights 24 also depends upon the size of the orifice through which it passes when departing the extruder. At the small orifice sizes of 0.015, 0.010, or even 0.005 inch, only a small amount of resin leaves the extruder over a period of time. The remainder backs up against the orifice opening and maintains the pressure upon the polymer in the pump section 23.

Larger orifices, of course, allow the pressure in the metering section 23 to dissipate. However, placing a screen, called a breaker plate, adjacent to the screw's working section 30 can retain a sufficient back pressure on the metering section 23. This screen can have a mesh of 100 or finer.

Placing additional obstacles in the path of the molten polymer beyond the breaker plate can also increase the presure experienced in the metering section 23. Furthermore, a longer land, which is the distance along which the bore of the extruder narrows down to the orifice size, can also retain the desired pressure in the flights 24. A pressure blender and a mixing head can also give increased pressure. An extruder with the appropriate modification can deliver the resin to its die under a pressure of 3,000 p.s.i. at the breaker plate.

Once produced, the material, as a thermoplastic, will submit to the usual product-forming techniques. Thus, it can undergo further extrusion to a particular shape, if not achieved in the original extrusion. Moreover, its thermoplastic nature allows the reuse of scraps of material and of rejected parts.

The present tubing can be used as medical grade tubing for clinical applications. The present tubing is particularly suitable for use in roller type heart pumps.

For use as a roller pump tubing, the preferred size is 0.375 inch, inside diameter, and 0.562 inch, outside diameter. A preferred formulation for such roller pump tubing is:

| Material components | Weight % |
| --- | --- |
| Kraton G-1651 (Shell Oil Co.) | 30.4 |
| Kraton G-1650 (Shell Oil Co.) | 7.6 |
| Polypropylene #5520 (Shell Oil Co.) | 3.0 |
| Polypropylene #5820 (Shell Oil Co.) | 13.0 |
| Polypropylene #467 DP (Eastman Corp.) | 2.0 |
| Silicone Oil #360 (Dow Corning) | 4.0 |
| Mineral Oil (Witco Chemical Co.) | 40.0 |
| Stabilizer-Irganox #1010 (Ciba-Geigy Corp.) | 0.05 |
| | 100.05 |

A description of the formation of the roller pump tubing is given in the Examples.

The present invention is further illustrated in the following non-limiting Examples.

EXAMPLE 1

A mixture having the following composition was prepared:

| Material | Weight % |
| --- | --- |
| Kraton G-1651 (Shell Oil Co.) | 30.4 |
| Kraton G-1650 (Shell Oil Co.) | 7.6 |
| Polypropylene 5520 (Shell Oil Co.) | 3.0 |
| Polypropylene 5820 (Shell Oil Co.) | 8.0 |
| Polypropylene 467 DP (Eastman Corp.) | 2.0 |
| Silicone Oil 360 (Dow Corning) | 4.0 |
| Mineral oil (Witco Chemical Co.) | 45.0 |
| Stabilizer-Irganox #1010 (Ciba-Geigy) | 0.05 |
| Total | 100.05 |

The mixture was fed into the hopper of a 2½ inch HPM extruder (HPM Corporation, Mt. Gilead, Ohio) and extruded under the following conditions:

| | |
|---|---|
| Draw-down ratio | approx. 10% |
| Zone 1 (feed zone) | 165.5° C. |
| Zone 2 (compression zone) | 171.1° C. |
| Zone 3 (metering zone) | 182.2° C. |
| Zone 4 (work zone) | 171.1° C. |
| Temperature at head | 168.3° C. |
| Temperature at die | 176.7° C. |

Screens were selected mesh of 40-60-80 stainless steel.

The tubing extrudate was passed into an open trough cooling chamber and pulled by a caterpillar-type puller. The extruder screw speed was 60 RPM and the line speed was 40 feet per minute. A tubing having a 0.375 inch inner diameter and 0.562 inch outer diameter was produced.

Physical properties of the extruded product:

| | Nominal | Minimum | Maximum |
|---|---|---|---|
| 1. Durometer, hardness instant ASTM D-2240 Shore A, Tolerance I3 | 50 | 47 | 53 |
| 2. Tensile properties PSI ASTM D-412 at 23° C.; Rate of 20 inch/minute. Bar (ASTM Part 35 D 638) Type V punched from 0.020" to 0.025" thick sheet | 1800 | 1500 | 2200 |
| 3. Ultimate elongation % ASTM D 412 | 850 | 800 | 1100 |
| 4. Specific gravity ±0.2 ASTM D-792 | 0.90 | 0.88 | 0.92 |
| 5. Melt Index ASTM-D 1238. Condition-E Gm/10 minute | 0.25 | 0.20 | 0.30 |

EXAMPLE 2

A mixture having the following composition was prepared:

| Material | Weight % |
|---|---|
| Kraton G-1651 (Shell Oil Co.) | 30.4 |
| Kraton G-1650 (Shell Oil Co.) | 7.6 |
| Polypropylene 5520 (Shell Oil Co.) | 3.0 |
| Polypropylene 5820 (Shell Oil Co.) | 13.0 |
| Polypropylene 467 DP (Eastman Corp) | 2.0 |
| Silicone Oil #360 (Dow Corning) | 4.0 |
| Mineral Oil (Witco Chemical Co.) | 40.0 |
| Stabilizer-Irganox 1010 (Ciba-Geigy) | 0.05 |
| Total | 100.05 |

The mixture was fed into the hopper of a 2½ inch HPM extruder and extruded under the following conditions:

| | |
|---|---|
| Draw-down ratio | approx. 10% |
| Zone 1 (feed zone) | 165.6° C. |
| Zone 2 (compression zone) | 171.1° C. |
| Zone 3 (metering zone) | 171.1° C. |
| Zone 4 (work zone) | 187.8° C. |
| Temperature at head | 176.7° C. |
| Temperature at die | 187.8° C. |

Screens were selected mest of 40-60-80 stainless steel. The extruder screw speed was 50 RPM annd the line speed was 44 feet per minute. The tubing extrudate was passed into an open trough cooling chamber and pulled by a caterpiller-type puller. A tubing having a 0.375 inch inner diameter and 0.562 inch outer diameter was produced.

Physical properties of the extruded product;

| | Nominal | Minimum | Maximum |
|---|---|---|---|
| 1. Durometer, hardness instant ASTM D-2240 Shore A, Tolerance ±3 | 60 | 57 | 63 |
| 2. Tensile properties PSI ASTM D-412 at 23° C. Rate of 20 inch/minute. Bar (ASTM Part 35 D-638 Type V) punched from 0.020" to 0.025" thick sheet | 2060 | 1760 | 2360 |
| 3. Ultimate elongation % ASTM D 792 | 670 | 540 | 800 |
| 4. Specific gravity ±0.02 ASTM D 792 | 0.90 | 0.88 | 0.92 |
| 5. Melt index ASTM-D 1238 Condition - E Gm/10 min. | 1.9 | 1.5 | 2.3 |

EXAMPLE 3

A mixture having the following formulation was prepared:

| Material | Weight % |
|---|---|
| Kraton G-1651 (Shell Oil Co.) | 27.6 |
| Kraton G-1650 (Shell Oil Co.) | 6.9 |
| Polypropylene 5520 (Shell Oil Co.) | 2.7 |
| Polypropylene 5820 (Shell Oil Co.) | 16.4 |
| Polypropylene 467 DP (Eastman Corp.) | 1.8 |
| Silicone Oil #360 (Dow Corning) | 3.6 |
| Mineral Oil (Witco Chemical Co.) | 40.9 |
| Stabilizer-Irganox 1010 (Ciba-Geigy) | 0.05 |
| Total | 99.95 |

The mixture was fed into the hopper of a 2½ inch HPM extruder and extruded under the following conditions:

| | |
|---|---|
| Draw-Down ratio | approx. 10% |
| Zone 1 (feed zone) | 176.7° C. |
| Zone 2 (compression zone) | 179.4° C. |
| Zone 3 (metering zone) | 179.4° C. |
| Zone 4 (work zone) | 182.2° C. |
| Temperature at head | 185.° C. |
| Temperature at die | °C. |

Screens were selected mesh of 40-60-80 stainless steel. The extruder screw speed was 60 RPM and the line speed was 40 feet per minute. The tubing extrudate was passed into an open trough cooling chamber and pulled by a caterpillar-type puller. A tubing having a 0.375 inch inner diameter and 0.562 outer diameter was formed.

Physical properties of the extruded product:

|  | Nominal | Minimum | Maximum |
|---|---|---|---|
| 1. Durometer, hardness instant ASTM D-2240 Shore A, Tolerance ±3 | 65 | 62 | 68 |
| 2. Tensile properties PSI ASTM D-412 at 23° C. Rate of 20 inch/minute. Bar (ASTM Part 35 D 638 Type V) punched from 0.020" to 0.025" thick sheet | 1900 | 1600 | 2300 |
| 3. Ultimate elongation % ASTM D 792 | 800 | 750 | 1050 |
| 4. Specific gravity ±0.02 ASTM D 792 | 0.90 | 0.88 | 0.92 |
| 5. Melt index ASTM-D 1238 Condition - E Gm/10 min. | 1.9 | 1.5 | 2.3 |

EXAMPLE 4

The experiments described in this Example were conducted at the Baylor College of Medicine, Houston, Tex.

The object of these experiments was to compare presently available polymeric tubings for use in roller type tubing-perfusion apparatus.

The tubings tested include the following:

| Material | Manufacturer |
|---|---|
| Polyvinyl chloride | Olson |
| Polyvinyl chloride | Travenol |
| Silicone rubber | Dow Corning |
| Silicone rubber | Sil-Med |
| Thermoplastic elastomer (this invention) | Concept, Inc. |

Three samples of each of the above-listed tubings were tested. Al tubings have an interior diameter of ½ inch.

Testing was performed at physiological flows and pressures on a roller pump mock circulatory loop using water as the fluid. Each tubing was tested under identical conditions. Pumping was continued for 30 days or until the tubing ruptured. Inlet pressure to the pump was 50 mm/Hg and flow was maintained at 4 liters per minute. Each tubing was rinsed for half an hour with double-filtered deionized water prior to the experiments. At the end of each twenty four hours of pumping, all water in the pump was suctioned through a 10 micron filter which was then examined microscopically, dried and weighed. Water in the Concept, Inc. tubing was fed to a 5 micron filter. Power requirements were measured by an ampmeter.

The tests were conducted to determine the following physical characteristics of the tubings:

(a) The number of cycles needed to rupture the tubing.
(b) The effects of pumping on the rebounding characteristics of the tubing as a function of time.
(c) The linearity of the rebounding characteristics of the tubing, i.e., the volume as a function of RPM.
(d) The amount of abrasion on the inner surface of the tubing caused by pumping.
(e) The amount of power that is required to pump in different types of tubing.

Figure 3:
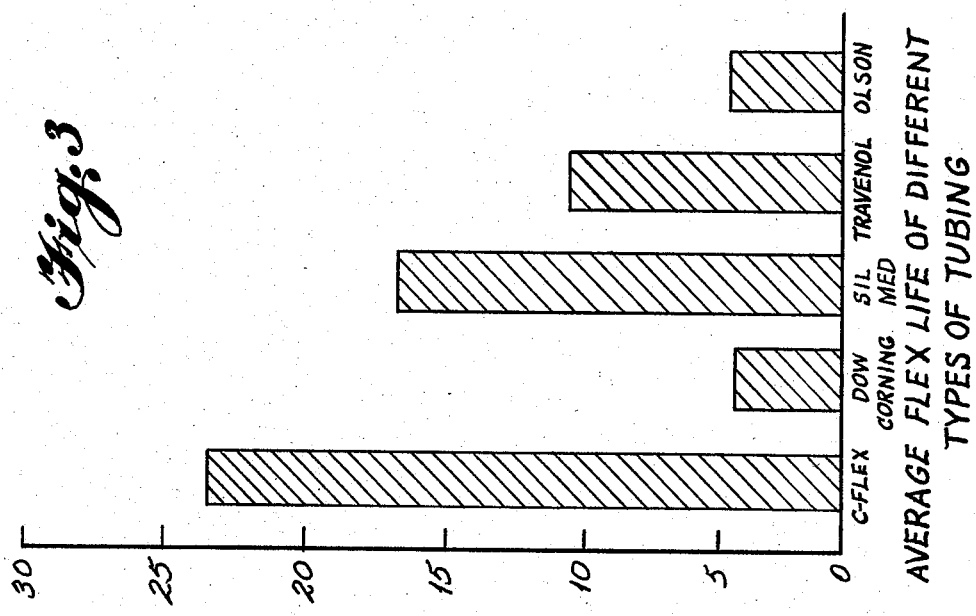
FIG. 3 shows the flex life of tubings tested in Example 4.

The results are summarized as follows:

(a) FIG. 3 shows the average day of rupture of each of the tubings tested. All ruptures occurred at the pump head.
(b) Rebounding over time, measured on a daily basis, remained constant in all tubings tested.
(c) Rebounding of tubing (volume vs RPM) with the rollers of the pump set at the proper occlusion indicates that there is a linear increase in pump output with increasing revolutions per minute in all tubings tested.
(d) Tubing debris produced by pumping generally known as spallation, from the tubings after pumping are shown in FIG. 4. The tubing formed of thermoplastic elastomeric composition showed the last amount of spallation. Large amounts of sticky black debris which adhere to all parts of the circulatory loop were noted for Bion. Microscopic studies of the 10 micron filter were conducted and found significant amounts of spallation with particles ranging from 1-2 mm in size, with the exception of the Concept, Inc. tubing. The weight of the particles collected on a daily basis was fairly consistent. Among the tubings tested, the thermoplastic elastomeric tubing of Concept, Inc. had the lowest spallation.
(e) The tubing of Concept, Inc. had the lowest power requirement 1 amp. as compared with 1.5 amp. or more for the other tubings.

The test results show that the thermoplastic elastomeric tubing of the present invention has the longest flex life and lowest spallation, which clearly indicate that this tubing has superior physical characteristics over the other tubings for use in cardiac assistance equipment.

EXAMPLE 5

In this Example, the hemocompatibility tests of the tubings listed in Example 4 were conducted on animals using a (heparinless) left heart roller pump bypass: Mongrel dogs weighing more than 19 kilograms were maintained under general endotracheal anesthesia. Exposure was via the left fifth intercostal space. Left ventricular, left atrial, pulmonary artery, femoral artery and central venous pressure were monitored. The left atrium was cannulated for bypass with 30 French Urethane USCI venous cannula and the descending thoracic aorta with a 20 French Urethane USCI arterial cannula. Siliconized metal connectors were used between the cannula and the tubing being tested. Continuous flow was maintained at 50-75 cc per kilogram per minute without heparin through the roller pump, the left atrial pressure being maintained between 0-5 mm/Hg. The pump run lasted six hours at which time the dogs were sacrificed. Plasma samples were drawn prior to the test and during pumping at 2.4 and 6 hours after test initiation. Autopsy of the dogs and examination of the tubing were conducted immediately. The heart, kidneys and brain were examined grossly and microscopically. Proper pump head occlusion was obtained for each tubing tested. After decannulation, the tubings were immediately drained of blood and examined. By proper occlusion, it is meant that a column of water 30 inches high is permitted to drop one inch per minute. For the half-inch tubings tested it appeared that after complete occlusion was attained, the desired fluid drop may be attained by opening the pump head by 0.003 inch.

Among the tubings tested, the thermoplastic elastomeric tubings of the present invention had the cleanest surfaces after six hours. Five of the eight dogs had thrombi in the kidneys. Among these five, two were fitted with the present thermoplastic elastomeric tubing. Plasma readily extracted phthalate type plasticizers from the vinyls. Trace amounts (5 ppm) of silicone were found in silicone plasma samples. The present tubings were found to be free of extractable matter. Both polyvinyl chloride and silicone rubber tubings yielded the highest concentration of spallation products.

The results in this Example also show that the thermoplastic elastomeric tubings of this invention are superior over the other tubings tested.

The results shown in Examples 4 and 5 clearly indicate that the present thermoplastic elastomeric tubing possesses the best results in mechanical, biological and toxicological testing.

What is claimed is:

1. A tubing formed of a polymeric composition comprising a thermoplastic elastomeric hydrocarbon block copolymer and a polysiloxane having a kinematic viscosity of 20 to $10^6$ centistokes at room temperature, the polysiloxane constituting from about 0.1 to 12 percent by weight of the composition, the balance being the copolymer.

2. The tubing of claim 1 wherein the copolymer comprises additionally up to 25% by weight of the composition polystyrene.

3. The tubing of claim 1 wherein the polymeric composition further comprises polypropylene which constitutes up to 45 percent by weight of the composition.

4. The tubing of claim 1 wherein the block copolymer has an A—B—A configuration where A is a monovinyl arene polymer block and B is a hydrogenated or nonhydrogenated conjugated diene polymer block.

5. The tubing of claim 4 wherein A comprises a styrene block and has a molecular weight of 5,000 to 40,000, and B comprises an ethylene-butylene block and has a molecular weight of 20,000 to 50,000.

6. The tubing of claim 5 wherein the total molecular weight of the polymeric composition ranges from 50,000 to 600,000.

7. The tubing of claim 6 wherein the polysiloxane has the repeating structure:

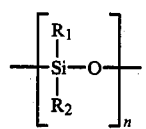

wherein $R_1$, $R_2$ = H, $CH_3$ or

and n is a positive integer ranging from 10 to 20,000.

8. A medical grade tubing for clinical use and formed of a polymeric composition comprising a thermoplastic elastomeric hydrocarbon block copolymer and a polysiloxane having a kinematic viscosity of 20 to $10^6$ centistokes at room temperature, the polysiloxane constituting from about 0.1 to 12 percent by weight of the composition, the balance being the copolymer.

9. The tubing of claim 8 wherein the copolymer comprises additionally up to 25% by weight of the composition polystyrene.

10. The tubing of claim 8 wherein the polymeric composition further comprises polypropylene which constitutes up to 45 percent by weight of the composition.

11. The tubing of claim 8 wherein the block copolymer has an A—B—A configuration where A is a monovinyl arene polymer block and B is a hydrogenated or nonhydrogenated conjugated diene polymer block.

12. The tubing of claim 8 wherein A comprises a styrene block and has a molecular weight of 5,000 to 40,000, and B comprises an ethylene-butylene block and has a molecular weight of 20,000 to 50,000.

13. The tubing of claim 8 wherein the total molecular weight of the polymeric composition ranges from 50,000 to 600,000.

14. The tubing of claim 8 wherein the polysiloxane has the repeating structure:

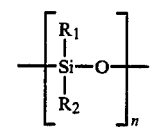

wherein $R_1$, $R_2$ = H, $CH_3$ or

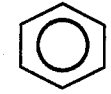

and n is a positive integer ranging from 10 to 20,000.

15. A tubing for cardiac assistance and formed of a polymeric composition comprising a thermoplastic elastomeric hydrocarbon block copolymer and a polysiloxane having a kinematic viscosity of 20 to $10^6$ centistokes at room temperature, the polysiloxane constituting from about 0.1 to 12 percent by weight of the composition, the balance being the copolymer.

16. The tubing of claim 15 wherein the copolymer comprises additionally up to 25% by weight of the composition polystyrene.

17. The tubing of claim 15 wherein the polymeric composition further comprises polypropylene which constitutes up to 45 percent by weight of the composition.

18. The tubing of claim 15 wherein the block copolymer has an A—B—A configuration where A is a monovinyl arene polymer block and B is a hydrogenated or nonhydrogenated conjugated diene polymer block.

19. The tubing of claim 15 wherein A comprises a styrene block and has a molecular weight of 5,000 to 40,000, and B comprises an ethylene-butylene block and has a molecular weight of 20,000 to 50,000.

20. The tubing of claim 8 wherein the total molecular weight of the polymeric composition ranges from 50,000 to 600,000.

21. The tubing of claim 15 wherein the polysiloxane has the repeating structure:

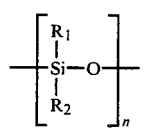
wherein $R_1$, $R_2$ = H, $CH_3$ or
and n is a positive integer ranging from 10 to 20,000.
* * * * *